United States Patent
Heilmann et al.

[11] Patent Number: 5,843,049
[45] Date of Patent: Dec. 1, 1998

[54] ARRANGEMENT FOR ADMINISTERING A MEDICAL FLUID

[75] Inventors: Klaus Heilmann, St. Wendel; Peter Friedrich, Saarbrüken; Claus Jessen, Otzenhausen; Josef Winter, Saarlouis, all of Germany

[73] Assignee: Fresenuis AG, Bad Homburg, Germany

[21] Appl. No.: 835,093

[22] Filed: Apr. 4, 1997

[30] Foreign Application Priority Data

Apr. 5, 1996 [DE] Germany .................. 196 13 678.4

[51] Int. Cl.⁶ .................................................. A61M 31/00
[52] U.S. Cl. ..................... 604/275; 206/483; 383/38; 604/410
[58] Field of Search ................... 604/275–278, 604/410, 257; 206/483; 383/38–40, 210, 211

[56] References Cited

U.S. PATENT DOCUMENTS

| | | | |
|---|---|---|---|
| 3,761,013 | 9/1973 | Schuster et al. | 229/62 |
| 4,270,533 | 6/1981 | Andreas | 604/410 |
| 4,576,603 | 3/1986 | Moss | 604/410 |
| 4,976,707 | 12/1990 | Bodicky et al. | 604/408 |
| 5,560,403 | 10/1996 | Balteau et al. | 141/9 |

FOREIGN PATENT DOCUMENTS

| | | |
|---|---|---|
| 0 118 114 | 9/1984 | European Pat. Off. . |
| 26 54 725 | 7/1977 | Germany . |
| WO 83/02061 | 6/1983 | WIPO . |

*Primary Examiner*—John D. Yasko
*Assistant Examiner*—Deborah Blyveis
*Attorney, Agent, or Firm*—Kenyon & Kenyon

[57] ABSTRACT

The invention relates to an apparatus for administering a medical fluid comprises a film-sheet pouch of a heat-sealed polymeric material, which includes a first chamber containing medical fluid and a second chamber for receiving used medical fluid, and comprises a cross-over conveying device detachably enclosed within a third chamber of the film-sheet pouch that includes a fluid conduit line, having a first end heat-sealed into the bonded seam defining the first chamber and a second end including a connector coupled to a peritoneal catheter. The apparatus of the present invention also includes at least one shut-off element to control the flow of fluid out of the first chamber into the conduit line.

7 Claims, 2 Drawing Sheets

ARRANGEMENT FOR ADMINISTERING A MEDICAL FLUID

FIELD OF THE INVENTION

The invention relates to an apparatus for administering a medical fluid employing a film-sheet pouch.

BACKGROUND OF THE INVENTION

Infusion bags are known, which are provided with a connector to couple the bag to a cross-over conveying device having a conduit tube with a shut-off element and a connector at its unattached end. In addition, infusion bags are used which have cross-over conveying devices attached thereto. The advantage of these devices for administering medical fluids lies in that no connector arrangement is provided for connecting the cross-over conveying device to the bag, so that the frequency of infection is reduced. To prevent microbic contamination of the cross-over conveying device, it is known to heat-seal the film-sheet bag, inclusive of the cross-over conveying device, in a separate overwrap bag which is formed and evacuated of air. The disadvantage associated with these devices is that the additional wrapping leads to increased manufacturing costs. Moreover, the overwrap bag must be disposed of after the device is used.

To perform transperitoneal dialysis, apparatuses are used to administer a medical fluid into the peritoneal cavity of a patient that not only comprise a fluid-filled pouch, but an empty pouch as well, to receive the used medical fluid following the transperitoneal dialysis. An apparatus of this kind is disclosed, for example, by European A-0 488 288.

DBP 1 129 258 describes a flexible plastic container for medical fluid having a pouch-type wrapping to close off a tubular connector in a sterile and seal-tight manner. The pouch-type wrapping is made of sealing strips that are layered flat, one upon the other, and imperviously enclose the protruding end of the connector. Both the sealing strips as well as the tubular connector are permanently heat-sealed to the pouch.

U.S. Pat. No. 4,183,434 describes a pouch for storing blood components, which has at least two inlets that are hermetically enclosed by pocket-like protective wrappings. To connect conduit tubes, these protective wrappings can be peeled open by pulling them apart.

U.S. Pat. No. 5,364,384 describes a film-sheet pouch that is separated into two chambers, the first chamber containing a medical fluid and the second chamber enclosing connection members of a port so as to wrap them in a sterilized manner. The second chamber can be peeled open by means of an extension portion to expose the connection members.

SUMMARY OF THE INVENTION

The underlying object of the invention is to create an apparatus for administering a medical fluid which is simple and cost-effective to manufacture and is protected from microbic contamination.

In the apparatus according to the present invention for administering a medical fluid, the sterile wrapping is formed by the pouch film-sheet itself. Thus, there is no need for an additional separate overwrap to prevent microbic contamination of the cross-over device. The apparatus according to the invention can be produced cost-effectively in a few steps, with a minimum of wrapping material being required. Moreover, by economizing on material, a reduction in weight can be achieved.

The film-sheet pouch according to the present invention has a first chamber containing a medical fluid, a second chamber for receiving used medical fluid, and a third chamber that accommodates a cross-over conveying device, so that all parts are sealingly enclosed. To use the apparatus according to the invention in transperitoneal dialysis to administer a medical fluid into the peritoneal cavity of the patient, the second chamber is in fluid communication with an unattached end of an outflow drainage line that branches off from a conduit tube of the cross-over conveying device. Used dialyzing fluid is directed into the second chamber.

The fluid-filled first chamber and the empty second chamber are formed by two sets of film-sheet layers which are sealingly bonded together, the outer film-sheet layers extending over the edge area of the inner film-sheets layers. The edge areas of the two outer film-sheet layers are sealingly bonded together, forming a third chamber that accommodates the cross-over conveying device. The inner film-sheet layers are layered flat upon each other. In an alternative specific embodiment, the pouch is comprised of three sets of film-sheet layers, where the innermost film-sheet sheet layers form a shared partition wall for a fluid-filled first chamber and an empty second chamber.

To remove the cross-over conveying device, it is necessary to open the third chamber of the film-sheet pouch. The chamber can be cut using, for example, a knife or scissors.

It is particularly advantageous when a circumferential bonded seam, which joins together the outer film-sheet layers, is peelable, at least over a portion of its length. That is, the superposed film-sheets are so bonded together along the seam so that the film-sheets can be separated without being destroyed. A peelable seam of this kind makes it possible to simply separate the film-sheet layers of the pouch by hand and to quickly remove the cross-over conveying device. To further simplify the opening of the pouch, tear tabs can also be provided. Optionally, the film-sheet layers can also be bonded together detachably, forming a narrow outer edge, making it possible to easily grip the film-sheet edges that are not bonded together.

DETAILED DESCRIPTION

Figure 1:
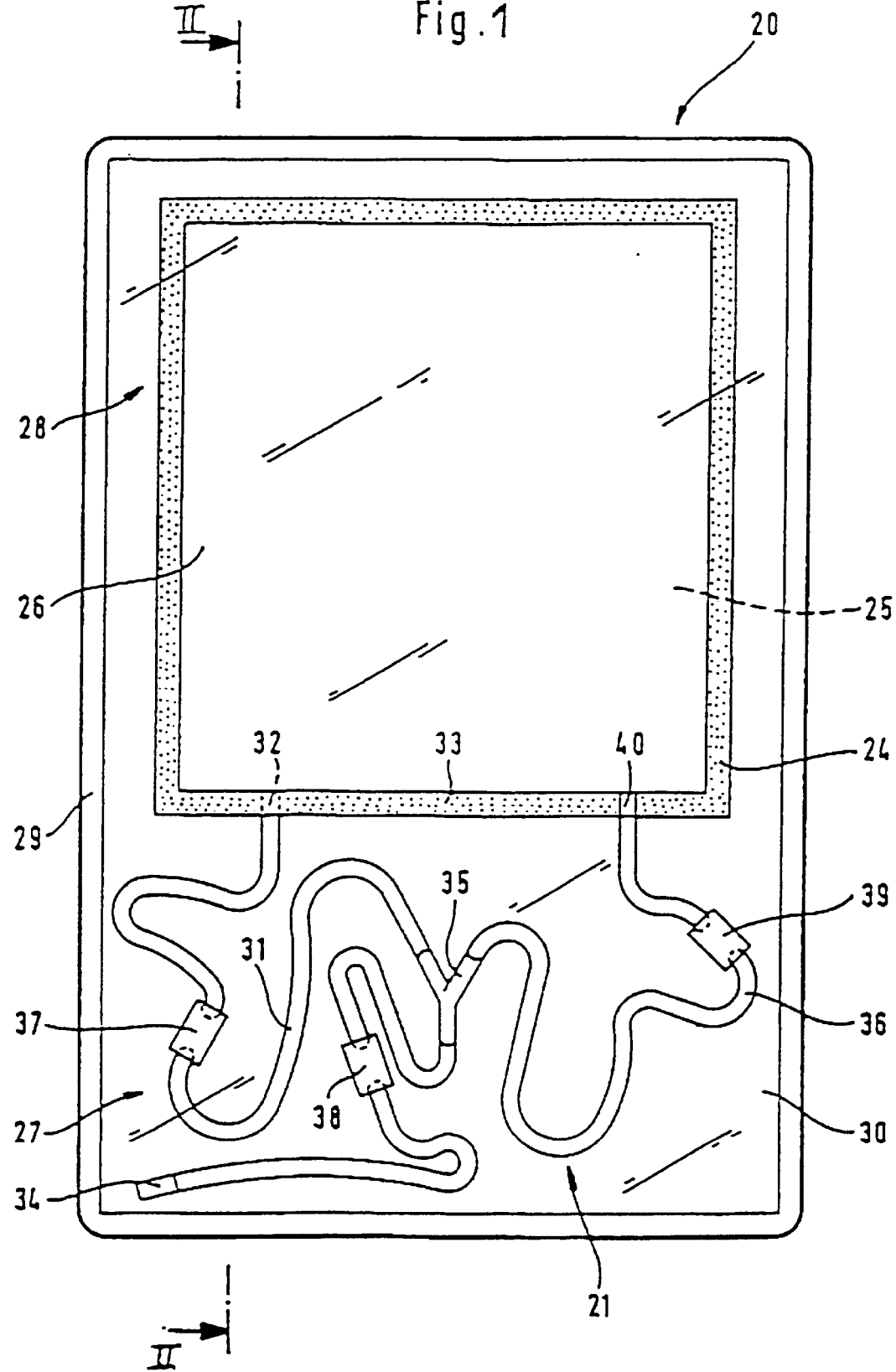
FIG. 1 shows a schematic representation of an apparatus for administering a medical fluid into the peritoneal cavity of the patient in accordance with the invention, comprising a fluid-filled first chamber, an empty second chamber, and a third chamber that accommodates the cross-over conveying device.
Figure 2:
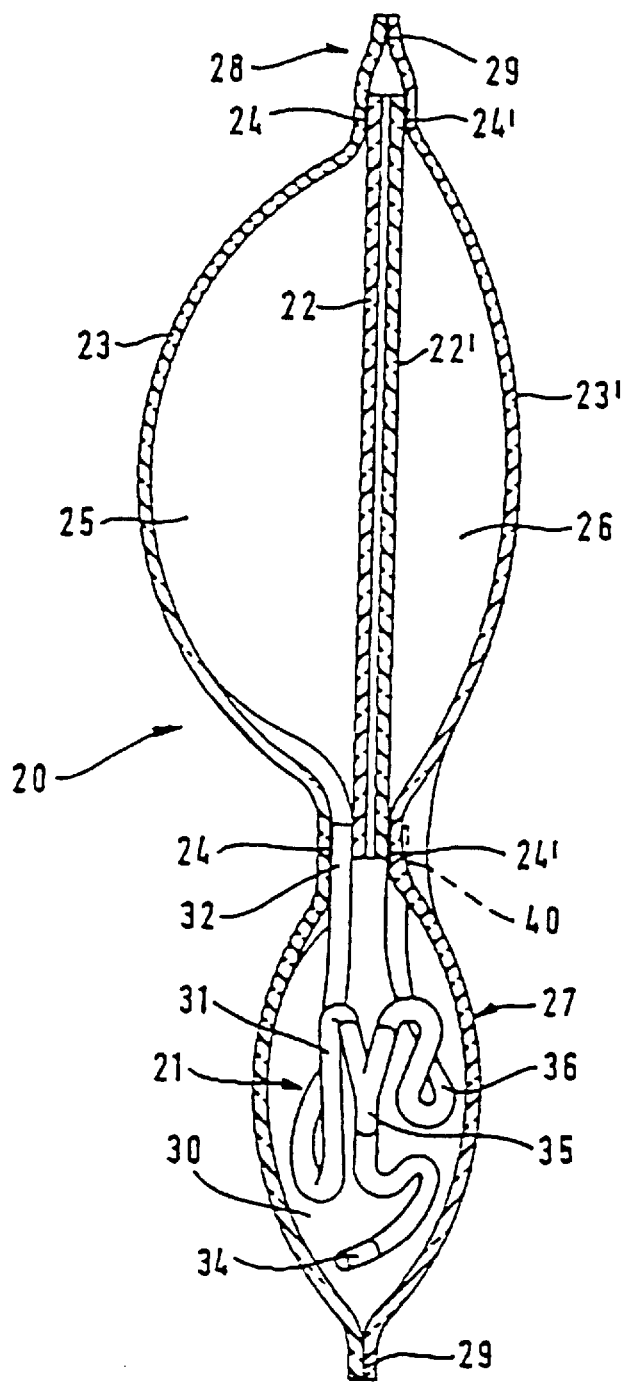
FIG. 2 shows a section through the apparatus of FIG. 1 along the line II—II, the film-sheets not being shown true-to-scale for the sake of clarity.

In a simplified, schematic representation, FIG. 1 illustrates an exemplary embodiment of a film-sheet pouch 20, comprising a cross-over conveying device 21 for administering a medical fluid into the peritoneal cavity of a patient. In this exemplary embodiment, film-sheet pouch 20 is designed as a three-chamber bag. It is comprised of four layered, rectangular film-sheets 22, 22' and 23, 23', which are sealingly bonded together, forming the three chambers as shown in FIG. 2. Film-sheets 22, 22' and 23, 23' are made of a polymeric material that is peelable following heat sealing.

The two outer film-sheets 23, 23' are dimensioned to extend over the edge area of the two inner film-sheets 22, 22'. The inner film-sheets 22, 22' are permanently bonded to the outer film-sheets 23 or 23' adjoining them, respectively.

Reference numerals 24, 24' designate the circumferential bonded seams in the outer edge areas of the inner film-sheets 22, 22'.

Together with inner film-sheet 22, the outer film-sheet denoted by reference numeral 23 forms a chamber 25, which is filled with a medical fluid, while the outer film-sheet provided with reference numeral 23' forms, together with inner film-sheet 22', an empty second chamber 26, which receives the medical fluid following a dialysis treatment.

Film-sheets 22, 22' and 23, 23' are so layered in the area of the bottom narrow side of the pouch so that the outer film-sheets 23, 23' overlap in one broad section 27. Apart from that, the projecting edge areas of the outer film sheets 23, 23' form only one narrow overlapping area 28. In the outer edge area, the outer film-sheets 23, 23' are heat-sealed with a peelable, circumferential bonded seam 29, forming a third chamber 30, which contains the cross-over conveying device 21 depicted in FIGS. 1 and 2.

Cross-over conveying device 21 has a conduit tube 31, having a first end 32 heat-sealed into lower section 33 of circumferential bonded seam 24 that defines fluid-filled first chamber 25. Therefore, conduit tube 31 is in fluid communication with the interior of first chamber 25. A second end of conduit tube 31 is provided with a connector 34 to facilitate attachment of a peritoneal catheter that is not situated in chamber 30.

Coupled by way of a Y-shaped, branched connector piece 35 to conduit tube 31 is a drain tube 36, whose unattached end 40 is heat-sealed into the lower section of the circumferential, bonded edge 24', which defines second chamber 26. Shut-off elements 37 and 38 are provided in the section of the conduit tube between first chamber 25 and the Y-shaped, branched connector piece 35, and in the section between the Y-shaped, branched connector piece 35 and connector 34 of conduit tube 31, respectively. Furthermore, a shut-off element 39 is provided in drain tube 36. Shut-off elements 37, 38 and 39 enable conduit tube 31 to be opened and drain tube 36 to be closed, so that the medical fluid can flow via connector 34 into the peritoneal catheter, shut-off elements 37, 38 and 39 also allow the top section of conduit tube 31 to be closed and drain tube 36 to be opened, so that the medical fluid can be directed out of the peritoneal catheter via the drain tube 36 into the second chamber 26.

To attach cross-over conveying device 21 to the peritoneal catheter, the two outer film-sheets 23, 23' are torn apart along peelable seam 29, enabling first chamber 25 and second chamber 26 to be separated from one another to expose the cross-over conveying device.

What is claimed is:

1. An apparatus for administering a medical fluid comprising:

a film-sheet pouch of a heat-sealed polymeric material including:

a first chamber for holding a medical fluid wherein the first chamber is defined by at least one bonded seam, a second chamber for receiving the medical fluid following a dialysis treatment wherein the second chamber is defined by at least one bonded seam, and a third chamber cooperating with the first and second chamber; and a cross-over conveying device detachably enclosed within the third chamber of the fluid sheet pouch, the cross-over conveying device having a conduit tube for receiving the medical fluid from the first chamber, wherein a first end of the conduit tube is heat-sealed into the at least one bonded seam defining the first chamber of the film-sheet pouch, and a second end of the conduit tube includes a connector for connecting the conduit tube to a catheter, and wherein the conduit tube is coupled to a first end of a drain tube, the drain tube having a second end heat-sealed into the at least one bonded seam defining the second chamber of the film-sheet pouch.

2. The apparatus according to claim 1, wherein the conduit tube is coupled to the first end of the drain tube by a branched connector piece.

3. The apparatus according to claim 2, wherein the conduit tube includes a first shut-off element between the second chamber and the branched connector piece, and a second shut-off element between the branched connector piece and the connector for connecting the conduit tube to a catheter.

4. The apparatus according to claim 1, wherein the drain tube includes a shut-off element for closing the drain tube and delivering the medical fluid from the first chamber to the catheter.

5. The apparatus according to claim 1, wherein the at least one bonded seam defining the third chamber is peelable at least over a portion of its length.

6. The apparatus according to claim 1, wherein the film-sheet pouch is formed from first and second outer film-sheet layers and first and second inner film-sheet layers wherein the first and second outer film-sheet layers extend over the first and second inner film-sheet layers, and wherein the first and second inner film-sheet layers are heat-sealed to the outer film-sheet layers to form the first chamber and the second chamber, and wherein the first and second outer film-sheet layers are sealingly bonded together at their outer edge areas to form the third chamber.

7. The apparatus according to claim 6, wherein the outer film-sheet layers are detachably bonded together to form a bonded seam having an outer edge for gripping the bonded seam to open the third chamber of the film-sheet pouch and remove the cross-over device.

* * * * *